(12) United States Patent
Keane et al.

(10) Patent No.: US 9,289,538 B2
(45) Date of Patent: *Mar. 22, 2016

(54) METHOD OF FORMING AND THE RESULTING MEMBRANE COMPOSITION FOR SURGICAL SITE PRESERVATION

(71) Applicant: DePuy Synthes Products, LLC, Raynham, MA (US)

(72) Inventors: Michael Keane, Downingtown, PA (US); William Miller, Downingtown, PA (US); Nigel Smith, Hertfordshire (GB)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/262,912

(22) Filed: Apr. 28, 2014

(65) Prior Publication Data
US 2014/0322288 A1 Oct. 30, 2014

Related U.S. Application Data

(63) Continuation of application No. 13/142,294, filed as application No. PCT/US2008/088444 on Dec. 29, 2008, now Pat. No. 8,748,508.

(51) Int. Cl.
| | |
|---|---|
| A61L 31/06 | (2006.01) |
| A61L 31/14 | (2006.01) |
| A61L 31/00 | (2006.01) |
| A61L 31/12 | (2006.01) |
| A61B 17/00 | (2006.01) |
| A61B 19/00 | (2006.01) |
| A61L 31/18 | (2006.01) |

(52) U.S. Cl.
CPC .......... *A61L 31/14* (2013.01); *A61L 31/06* (2013.01); *A61L 31/129* (2013.01); *A61L 31/145* (2013.01); *A61L 31/18* (2013.01)

(58) Field of Classification Search
None
See application file for complete search history.

(56) References Cited

U.S. PATENT DOCUMENTS

| | | | | |
|---|---|---|---|---|
| 3,867,939 | A * | 2/1975 | Moore et al. | 604/291 |
| 4,135,021 | A * | 1/1979 | Patchell et al. | 428/134 |
| 4,275,105 | A * | 6/1981 | Boyd et al. | 428/198 |
| 4,287,251 | A * | 9/1981 | King et al. | 428/198 |
| 4,638,796 | A * | 1/1987 | Sims | 602/45 |
| 5,007,916 | A | 4/1991 | Linsky et al. | |
| 5,047,055 | A * | 9/1991 | Bao et al. | 623/17.16 |
| 5,260,066 | A * | 11/1993 | Wood et al. | 424/447 |
| 5,288,503 | A * | 2/1994 | Wood et al. | 424/497 |
| 5,508,317 | A | 4/1996 | Muller | |
| 5,578,045 | A * | 11/1996 | Das | 606/151 |
| 5,681,579 | A * | 10/1997 | Freeman | 424/448 |
| 5,795,584 | A | 8/1998 | Totakura et al. | |
| 5,846,214 | A * | 12/1998 | Makuuchi et al. | 602/52 |
| 5,981,826 | A * | 11/1999 | Ku et al. | 623/23.72 |
| 6,077,281 | A * | 6/2000 | Das | 606/151 |
| 6,164,702 | A | 12/2000 | Hauber et al. | |
| 6,264,702 | B1 | 7/2001 | Ory et al. | |
| 6,271,278 | B1 | 8/2001 | Park et al. | |
| 6,638,917 | B1 | 10/2003 | Li et al. | |
| 6,693,089 | B1 | 2/2004 | Li et al. | |
| 6,846,291 | B2 | 1/2005 | Smith et al. | |
| 6,981,944 | B2 * | 1/2006 | Jamiolkowski et al. | 600/30 |
| 6,991,837 | B2 | 1/2006 | Klein et al. | |
| 7,214,245 | B1 * | 5/2007 | Marcolongo et al. | 623/17.16 |
| 7,235,592 | B2 | 6/2007 | Muratoglu et al. | |
| 7,247,370 | B2 | 7/2007 | Childs et al. | |
| 7,316,817 | B2 | 1/2008 | Matloub et al. | |
| 7,316,919 | B2 | 1/2008 | Childs et al. | |
| 8,287,595 | B2 * | 10/2012 | Vresilovic et al. | 623/17.12 |
| 8,748,508 | B2 | 6/2014 | Keane et al. | |
| 2002/0064558 | A1 | 5/2002 | Tanaka et al. | |
| 2003/0162841 | A1 | 8/2003 | Pathak et al. | |

(Continued)

FOREIGN PATENT DOCUMENTS

| | | |
|---|---|---|
| JP | 08-266615 | 10/1996 |
| JP | 2008-264266 A | 11/2008 |

(Continued)

OTHER PUBLICATIONS

[No Author Listed] Cardiovascular implants—Tubular vascular prostheses. American National Standard. AAMI, 2001, 56 pages.
[No Author] Delstar HealthCare Products, Delstar Technolgies, 2004.
International Search Report for corresponding Appln. No. PCT/US08/088444, dated Sep. 14, 2009.
[No Author Listed] Consensus in adhesion reduction management. The Obstetrician an Gynaecologist. Supplemental 2004, 6(S2):1-16.

(Continued)

*Primary Examiner* — Peter A Salamon
(74) *Attorney, Agent, or Firm* — Nutter McClennen & Fish LLP

(57) ABSTRACT

A method of forming and the resulting membrane composition for securement to a patient's bone or tissue to reduce the formation of tissue adhesions following a surgical procedure comprises a first component and a second component. The first component comprises a hydrogel including at least one crosslinked polymer. The second component comprises a textile component. The composition has a thickness between about two tenths of a millimeter (0.2 mm) to about six tenths of a millimeter (0.6 mm), a suture retention strength between about one Newton (1 N) to about thirteen Newtons (13 N), a static coefficient of friction between about one hundredth (0.01) and about one-half (0.5), a kinetic coefficient of friction between about one hundredth (0.01) and about one-half (0.5) and a flexibility of less than thirty millimeters (30 mm) bend length. A method of reducing the occurrence of tissue adhesions following surgery comprises applying the membrane composition to a surgical site.

18 Claims, 8 Drawing Sheets

(56) References Cited

U.S. PATENT DOCUMENTS

| | | |
|---|---|---|
| 2003/0225355 A1 | 12/2003 | Butler |
| 2004/0049187 A1 | 3/2004 | Burnett et al. |
| 2004/0091603 A1 | 5/2004 | Priewe |
| 2004/0097807 A1 | 5/2004 | Smith et al. |
| 2004/0115241 A1 | 6/2004 | Calhoun et al. |
| 2005/0084514 A1 | 4/2005 | Shebuski et al. |
| 2005/0095296 A1* | 5/2005 | Lowman et al. ............ 424/486 |
| 2006/0067976 A1 | 3/2006 | Ferraro et al. |
| 2006/0078586 A1 | 4/2006 | Ferraro et al. |
| 2006/0116696 A1 | 6/2006 | Odermatt et al. |
| 2006/0204738 A1 | 9/2006 | Dubrow et al. |
| 2007/0073402 A1* | 3/2007 | Vresilovic et al. ......... 623/17.12 |
| 2007/0111937 A1 | 5/2007 | Pickar et al. |
| 2007/0280990 A1 | 12/2007 | Stopek |
| 2008/0118550 A1 | 5/2008 | Martakos et al. |
| 2008/0206305 A1 | 8/2008 | Herweck et al. |
| 2011/0270286 A1 | 11/2011 | Keane et al. |

FOREIGN PATENT DOCUMENTS

| | | |
|---|---|---|
| WO | 97/07833 A2 | 3/1997 |
| WO | 02/34304 A1 | 5/2002 |
| WO | 02/102425 A2 | 12/2002 |

OTHER PUBLICATIONS

Bourke et al., A photo-crosslinked poly(vinyl alcohol) hydrogel growth factor release vehicle for wound healing applications. AAPS PharmSci. Dec. 4, 2003;5(4):E33.

Cohen et al., Effects of implant material and plate design on tendon function and morphology. Clin Orthop Relat Res. Apr. 2006;445:81-90.

Fogel et al., Surgical treatment of dysphagia after anterior cervical interbody fusion. Spine J. Mar.-Apr. 2005;5(2):140-4.

Fung et al., Biomechanics: Motion, Flow, Stress and Growth. Springer-Verlag, New York,p. 455, 1990.

Gustafsson et al., MRI of the knee after locked unreamed intramedullary nailing of tibia. Chir Organi Mov. Jan. 2008;91(1):45-50. doi: 10.1007/s12306-007-0008-1. Epub Feb. 10, 2008.

Hiraizumi et al., Application of polyvinyl alcohol hydrogel membrane as anti-adhesive interposition after spinal surgery. Spine (Phila Pa 1976). Nov. 1, 1995;20(21):2272-7.

International Preliminary Report on Patentability for Application No. PCT/US2008/088444, mailed Jun. 29, 2011 (7 pages).

Kato et al., Evaluation of hyaluronic acid sheet for the prevention of postlaminectomy adhesions. Spine J. Sep.-Oct. 2005;5(5):479-88.

Kobayashi et al., Development of polyvinyl alcohol-hydrogel (PVA-H) shields with a high water content for tendon injury repair. J Hand Surg Br. Oct. 2001;26(5):436-40.

Lang et al., Polyvinyl alcohol gel prevents abdominal adhesion formation in a rabbit model. Fertil Steril. Oct. 2007;88(4 Suppl):1180-6. Epub May 4, 2007.

Liakakos et al., Peritoneal adhesions: etiology, pathophysiology, and clinical significance. Recent advances in prevention and management. Dig Surg. 2001;18(4):260-73.

Matsuda et al., Evaluation of the antiadhesion potential of UV crosslinked gelatin films in a rat abdominal model. Biomaterials. Jul. 2002;23(14):2901-8.

Matsumura et al., Novel anti-adhesive pericardial substitute for multistage cardiac surgery. Asian Cardiovasc Thorac Ann. Aug. 2008;16(4):309-12.

Menzies, D., Postoperative adhesions: their treatment and relevance in clinical practice. Ann R Coll Surg Engl. May 1993;75(3):147-53.

Mohsenipour et al., Prevention of local scar formation after operative discectomy for lumbar disc herniation. Acta Neurochir (Wien). 1998;140(1):9-13.

Nguyen et al., Anterior exposure of the spine for removal of lumbar interbody devices and implants. Spine (Phila Pa 1976). Oct. 1, 2006;31(21):2449-53.

Park et al., Swelling and mechanical properties of glycol chitosan/poly(vinyl alcohol) IPN-type superporous hydrogels. J Biomed Mater Res A. Sep. 15, 2006;78(4):662-7.

Ramires et al., Biocompatibility of poly(vinyl alcohol)-hyaluronic acid and poly(vinyl alcohol)-gellan membranes crosslinked by glutaraldehyde vapors. J Mater Sci Mater Med. Jan. 2002;13(1):119-23.

Razzak et al., The characterization of dressing component materials and radiation formation of PVA-PVP hydrogel. Radiation Physics and Chemistry. Jun. 1999, vol. 55, Issue 2, pp. 153-165.

Razzak et al., Irradiation of polyvinyl alcohol and polyvinyl pyrrolidone blended hydrogel for wound dressing. Radiation Physics and Chemistry. Jul. 2001, vol. 61, Issue 1, pp. 107-113.

Seeger et al., Prevention of postoperative pericardial adhesions using tissue-protective solutions. J Surg Res. Feb. 15, 1997;68(1):63-6.

Thomas et al., Novel associated hydrogels for nucleus pulposus replacement. J Biomed Mater Res A. Dec. 15, 2003;67(4):1329-37.

Walther et al., A novel adhesion barrier facilitates reoperations in complex congenital cardiac surgery. J Thorac Cardiovasc Surg. Feb. 2005;129(2):359-63.

Weis et al., Poly(vinyl alcohol) membranes for adhesion prevention. J Biomed Mater Res B Appl Biomater. Aug. 15, 2004;70(2):191-202.

Weis et al., A-part gel—an efficient adhesion prevention barrier. J Biomed Mater Res B Appl Biomater. Jul. 2007;82(1):174-82.

Yucel et al., Histological evaluation of changes in the temporomandibular joint after direct and indirect trauma: an experimental study. Dent Traumatol. Aug. 2002;18(4):212-6.

* cited by examiner

METHOD OF FORMING AND THE RESULTING MEMBRANE COMPOSITION FOR SURGICAL SITE PRESERVATION

CROSS-REFERENCE TO RELATED APPLICATIONS

The present application is a continuation of U.S. patent application Ser. No. 13/142,294 filed on Jun. 27, 2011, which is a national stage entry pursuant to 35 U.S.C. §371 of International Patent Application No. PCT/US2008/088444 filed on Dec. 29, 2008. These references are hereby incorporated by reference herein in their entireties.

FIELD OF THE INVENTION

The present invention relates to a method of forming, and the resulting membrane composition that functions as a barrier to preserve a surgical site and/or plane and minimize bodily tissue adhesions that may form after medical procedures.

BACKGROUND OF THE INVENTION

In surgical procedures, the steps involved in dissection, cauterization, suturing, etc. cause trauma to surrounding tissue and initiate the formation of local post surgical adhesions.

After surgical procedures such as anterior access spine surgery, general abdominal and pelvic surgery, cardiothoracic surgery, etc., a wound repair process begins in which scar tissue is laid down that disrupts the normal anatomic planes and results in soft tissue adhesions. These adhesions can cause post operative pain, bowel obstructions, and other complications. Further, upon revision surgery this scar tissue can cause a nearly blind navigation field and present challenges with mobilization of scarred down tissues (i.e., tissues that have adhered to nearby soft tissues, bone tissues or surgical implants). Vessel damage, nerve damage, and other soft tissue injury can be a hazard upon revision surgery.

After trauma surgery adhesions can form at the fracture site due to bone spurs or by attachments to the titanium or stainless steel plates or screws. These adhesions with surrounding tissues can cause post-operative complications such as tendon irritations, loss of tendon mobilization, and impaired local joint function. Further, these adhesions can cause challenges (and may result in surgical complications) during a subsequent hardware removal procedure.

In anterior access spine surgery, such as total disc arthroplasty, anterior lumbar interbody fusion and anterior plating, the soft tissue and blood vessels in front of the spine are mobilized during the access portion of the surgery. After the procedure, these vessels typically scar down (i.e., adhere) to the surgical site. These adhesions of the vessels increase the risk of vascular injury if a revision procedure needs to be performed. The incidence of vascular injury on revision surgical cases has been reported to be as high as fifty-seven percent (57%). A barrier device in these applications would serve two functions, first as a covering to protect the vessels from the hardware used in the spinal procedure and second as a guide and plane of dissection during the revision procedures to help remobilize the vessels.

In other spine applications a barrier can be useful as well. For example, in scoliosis treatment with growing rod procedures, it may be useful to prevent the growth of tissue onto the screws that will need to be accessed during the subsequent lengthening procedures. In cervical procedures a barrier could prevent adhesions from the esophagus to the spinal implants and surgical site in order to prevent complications such as dysphasia, irritations and erosion of the esophagus. In posterior spinal procedures, a barrier device can function as a dura repair or help to limit nerve root tethering post discectomy.

In cardiothoracic surgery, a barrier device can function to help facilitate re-operations for cardiac patients, by minimizing adhesion formations between the sternum and other tissues.

Similar challenges with adhesions have been described in general abdominal pelvic surgery as well as other surgical treatments.

BRIEF SUMMARY OF THE INVENTION

The present invention relates to a method of forming and the resulting membrane composition that functions as a barrier to preserve the surgical site and/or plane and prevent surgically induced adhesions.

One embodiment of the present invention may comprise a membrane composition for securement to a patient's bone or soft tissue to reduce the formation of tissue adhesions following a surgical procedure comprising a first component and a second component. The first component comprises a hydrogel including at least one crosslinked polymer. The second component comprises a textile component, wherein the membrane composition has a thickness between about two tenths of a millimeter (0.2 mm) to about six tenths of a millimeter (0.6 mm), a suture retention strength between about one Newton (1 N) to about thirteen Newtons (13 N), a static coefficient of friction between about one one-hundredth (0.01) and about one-half (0.5), a kinetic coefficient of friction between about one one-hundredth (0.01) and about one-half (0.5) and a flexibility of less than thirty millimeters (30 mm) bend length.

Another embodiment of the present invention may comprise a membrane composition for securement to a patient's bone or tissue comprising a first component and a second component. The first component comprises a hydrogel including at least one polymer selected from the group consisting of poly(vinyl alcohol), poly(vinyl pyrrolidone), poly(hydroxyethylmethacrylate), poly(acrylamide), poly(acrylic acid), poly(acrylonitrile), polyethylene imine and poly(ethylene glycol), wherein the at least one polymer is crosslinked. The second component comprises a textile component. The composition has sufficient thickness, suture retention strength, friction coefficient and flexibility to reduce the formation of tissue adhesions following a surgical procedure.

A further embodiment of the present invention may comprise a membrane for use as a surgical implant comprising a first component and a second component. The first component comprises a hydrogel including at least two polymers selected from the group consisting of poly(vinyl alcohol), poly(vinyl pyrrolidone), poly(hydroxyethylmethacrylate), poly(acrylamide), poly(acrylic acid), poly(acrylonitrile), polyethylene imine and poly(ethylene glycol), and the second component is selected from the group consisting of polypropylene, polyester, polyetheretherketone and expanded polytetrafluoroethylene. The textile component is formed of fibers having a thickness from about two hundredths of a millimeter (0.02 mm) to about three millimeters (3.00 mm). The fibers form pores from about fifteen thousandths of a millimeter (0.015 mm) to about twelve and seven tenths millimeters (12.7 mm) in size and the textile component is encapsulated by the first component. The membrane has a thickness between about two tenths of a millimeter (0.2 mm) and about six tenths of a millimeter (0.6 mm).

A further embodiment of the present invention may comprise a method of reducing the occurrence of tissue adhesions following surgery comprising applying a membrane composition comprising a first component and a second component, wherein the first component comprises a hydrogel including at least one crosslinked polymer, the second component comprises a textile component, wherein the composition has a thickness between about two tenths of a millimeter (0.2 mm) to about six tenths of a millimeter (0.6 mm), a suture retention strength between about one Newton (1 N) to about thirteen Newtons (13 N), a water content between about fifty percent (50%) and about eighty percent (80%) and a flexibility of less than thirty millimeters (30 mm) bend length to a patient's bone or tissue.

BRIEF DESCRIPTION OF THE DRAWINGS

The foregoing summary, as well as the following detailed description of the preferred embodiments of the application, will be better understood when read in conjunction with the appended drawings. The drawings, examples and embodiments described within this specification are to be understood as illustrative and exemplary of structures, features and aspects of the present invention and not as limiting the scope of the invention. It should be understood that the application is not limited to the precise arrangements and instrumentalities shown. In the drawings.

DETAILED DESCRIPTION OF THE INVENTION

Figure 1A:
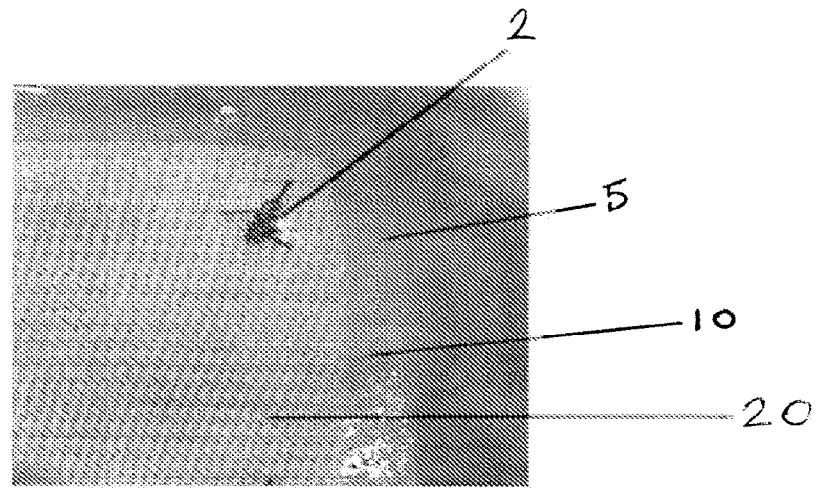
FIG. 1A shows a top plan view of a first preferred embodiment of a portion of a membrane composition of the present invention held in place by a suture.

The methods, examples and embodiments described within this specification are to be understood as illustrative and exemplary of structures, features and aspects of the present invention and not as limiting the scope of the invention. Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

A thin membrane to act as a barrier to preserve a tissue site and/or plane between implanted surgical devices and surrounding tissue or between apposing tissues that may form together after surgeries causing complications would be desirable and useful. It is further desired that the barrier be made of a biocompatible and stable material that has the appropriate material and mechanical properties to help facilitate placement. A strong, flexible, and thin material is preferred that can conform and drape over plates or be contoured to specific patient anatomy while still having sufficient strength to allow for fixation and to remain in place throughout the healing process. It is also desirable that the barrier exhibit sufficient lubricity to inhibit tissue adhesion formation while also having sufficient "stickiness" to allow for ease of placement during a surgical procedure.

It is also desirable that the barrier be formed of a compliant non-absorbable sheet like material with low porosity to prevent tissue in-growth or cellular penetration. It is preferred that the barrier be formed of a permanent and nonabsorbable thin material that will remain stable and not decompose after a length of time in a patient to thereby facilitate a potential revision procedure by providing a plane of dissection. Finally, it will be desirable that the barrier provide a navigation function during revision surgeries by the inclusion of separate and distinct markings with the option to make such markings radiopaque.

Figure 1B:
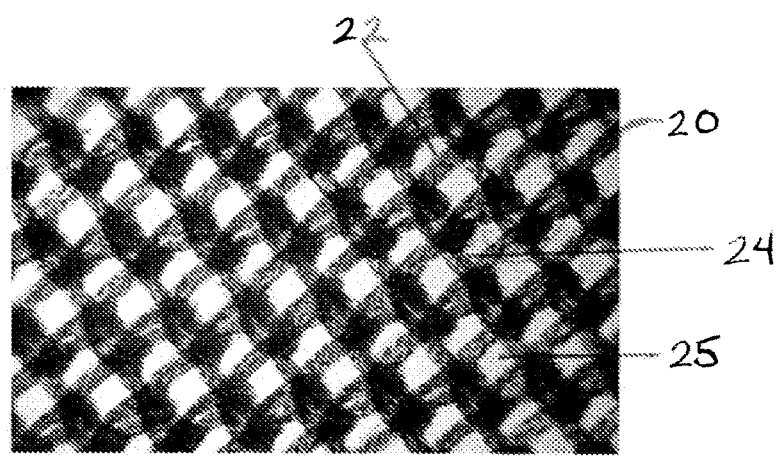
FIG. 1B shows a magnified top plan view of a textile component of the membrane composition shown in FIG. 1A.
Figure 1C:
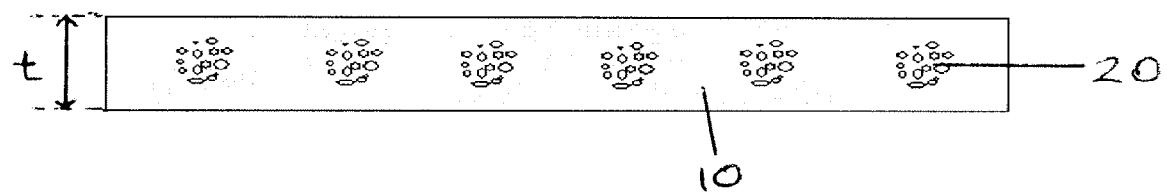
FIG. 1C shows a cross-sectional view of the membrane composition of FIG. 1A.

One embodiment of the barrier may comprise a membrane composition 5 comprising a first component 10 and a second component 20, wherein the first component 10 comprises a hydrogel including at least one crosslinked polymer and the second component 20 comprises a textile component, a base substrate or a filler biomaterial. The first component 10, also referred to as the matrix in this example, may be a hydrogel component that may be either chemically crosslinked to the base substrate, such as, for example, a filler or a mesh, or physically intertwined with the base substrate during the manufacturing process. The base substrate may be created from common surgical textiles that are either woven, knit, or braided. Various materials may function as the base substrate such as, for example, common surgical textile materials such as, but not limited to, polyester, expanded polytetrafluoroethylene (ePTFE), polyetheretherketone (PEEK), polyethylene (PE), and polypropylene (PP). The hydrogel component may provide the membrane composition with its lubricious characteristics. The textile component may provide increased strength to allow the membrane component to be attached to soft tissue, bone tissue or a surgical implant. The increased strength of the membrane composition also allows it to bear a load such as, for example, compression from an adjacent organ in a patient. FIG. 1A shows a preferred membrane composition 5 of the present invention held in place by a suture 2. The first component 10, encapsulates the second component 20. FIG. 1B shows an exemplary textile component of a membrane composition having courses 22, wales 24 and pores 25. FIG. 1C shows a cross-section of a membrane composition having a thickness t.

One embodiment of the present invention may comprise a membrane composition 5 comprising a first component 10 comprising a hydrogel including at least one crosslinked polymer, including, but not limited to, poly(vinyl alcohol) (PVA), poly(vinyl pyrollidone) (PVP), poly(hydroxyethylmethacrylate) (pHEMA), poly(acrylamide) (PAm), poly (acrylic acid) (PAA), poly(acrylonitrile) (PAN), polyethylene imine (PEI) or poly(ethylene glycol) (PEG). The hydrogel component 10 may have polymer concentrations ranging from about five percent (5%) to about sixty percent (60%) prior to combining with the base substrate, preferably about eight percent (8%) to about thirty-two percent (32%), more preferably about eleven and one-half percent (11.5%) to about twenty percent (20%). The creation of a spinal implant comprised of a PVA-based hydrogel is disclosed in U.S. Pat. No. 7,214,245, which is incorporated herein by reference.

Another embodiment of the present invention may comprise a membrane 5 composition comprising a first component 10 comprising a PVA-based hydrogel, wherein the PVA may be crosslinked to a second polymer including, but not limited to, PVP, pHEMA, PAm, PAA, PAN, PEI or PEG. The ratio of PVA to second polymer may range from about 1:1 to about 200:1, preferably about 5:1 to about 150:1, more preferably about 75:1 to about 110:1.

A further embodiment of the present invention may comprise a membrane composition 5 comprising a second component 20 which may comprise a textile component. The textile component 20 may be based on a surgical textile. Surgical textiles may be made from a variety of monofilament or multifilament materials such as, for example, but not limited to, polypropylene, polyester, PEEK, ePTFE or other permanent textile materials. The textile component may be mesh or felt or other constructs and made in a variety of manners such as, but not limited to, braiding, knitting, or weaving. The textile component 20 may have a linear density from about thirty (30) denier to about three hundred (300) denier. The knit versions may have courses 22 per inch ranging from about two (2) to about two hundred (200) courses per inch, preferably between about forty (40) to about one hundred ten (110) courses per inch and more preferably between about sixty (60) to about eighty (80) courses per inch. The knit versions may have wales 24 per inch values ranging from about two (2) to about one hundred (100) wales per inch, preferably between about twenty-five (25) to about sixty (60) wales per inch, more preferably thirty-six (36) to about forty-five (45) wales per inch. The thickness of the textile component or base substrate may range from about two hundredths of a millimeter (0.02 mm) to about three millimeters (3.00 mm), preferably between about nine hundredths of a millimeter (0.09 mm) to about one and two tenths millimeters (1.2 mm), more preferably about one tenth of a millimeter (0.1 mm) to about two tenths of a millimeter (0.2 mm). The pores 25 in the textile component may range from about fifteen thousandths of a millimeter (0.015 mm) to about twelve and seven tenths millimeters (12.7 mm) in order to provide an interlocking with the gel matrix. Preferably the pores in the textile component range from about five hundredths of a millimeter (0.05 mm) to about five and seven tenths millimeters (5.7 mm), more preferably two tenths of a millimeter (0.2 mm) to about three tenths of a millimeter (0.3 mm).

Another embodiment of the present invention may comprise a membrane composition capable of being stored in a variety of media such as, for example, but not limited to, phosphate buffered saline (PBS) solutions, aqueous polymer solutions, aqueous ionic solutions, pH specified solutions, antimicrobial solutions, or protein-containing solutions for drug delivery applications.

Another embodiment of the invention may comprise a method for forming the membrane composition 5. The hydrogel component 10 may be first made into a solution and then applied, rolled, or molded with the textile component 20. The at least one polymer of the hydrogel component 10 may be crosslinked in a variety of manners. The hydrogel component 10 may be molded and then chemically crosslinked by radiation or chemical means. The hydrogel component 10 may be only physically crosslinked in a variety of manners such as, for example, but not limited to, cryogelation (i.e., freezing and thawing), dehydration processing, or by mixing of the components in the manner of Theta gels (i.e., preparation of a stable gel formulation by competitively removing excess solvent (e.g., water) using a further component which has a higher affinity for the solvent than the hydrogel component). A combination of any of the crosslinking methods may be combined in which the hydrogel component 10 is first physically crosslinked and then chemically crosslinked, such as, for example, by electron beam ultra violet or visible radiation or gamma irradiation. After or during the crosslinking methods the hydrogel component 10 may be packed in a sterile barrier system with an appropriate storage media.

The embodiments of the present invention preferably provide superior surgical handling properties when compared to standard surgical membranes that are often too weak for adequate fixation or have "Saran Wrap" like qualities that make placement a challenge. The preferred membrane composition 5 of the present invention may be made very thin yet provide sufficient strength to allow for suture or tack fixation. Suture strength is valuable in order to reliably fasten the membrane composition to soft tissue or bone during a surgical procedure. Preferred membrane compositions 5 of the present invention may have a suture retention strength ranging from about one Newton (1 N) to about thirteen Newtons (13 N), preferably from about four Newtons (4 N) to about nine Newtons (9 N), more preferably from about six Newtons (6 N) to about seven Newtons (7 N).

In addition, the membrane composition 5 of the preferred embodiment may be made to be very flexible so that the barrier may contour or drape over plates or anatomical structures without or by minimizing wrinkling or bubbling of the membrane composition 5. It is preferred that the flexibility of the membrane composition 5 of the present invention be less than thirty millimeters (30 mm) bend length and less than 10 gram millimeters (10 g·mm) bending rigidity. Further, the surface of the membrane composition 5 may be a hydrogel that emits surface water throughout the surface of the membrane composition 5 in order to act with a slight surface tension (i.e., for example, to provide similar or equivalent surface energy to that of natural tissues to provide or promote a slight surface tension) allowing the product to temporarily stick to tissue and metal during procedural placement. This surface tension effect helps with arrangement of the barrier and because the gel is hydrophilic, and thus carrying its own surface water, this effect also occurs on dry surfaces such as, for example, surgical retractors, plates, pedicle screws, spinal rods, etc. The preferred membrane composition 5 of the present invention may also be sufficiently transparent to assist in identification of structures beneath the membrane composition 5 during placement. Additionally, the membrane composition 5 may be stretchable and mimic soft tissue characteristics by establishing, for example, large strains under small loads that allows the flexible material to further contour and bend with surrounding soft tissue structures during and/or after placement.

The preferred membrane composition 5 of the present invention may be biocompatible and have long term stability in vivo. The preferred membrane composition 5 of the present invention may provide for a low porosity surface that limits tissue in-growth and cellular penetration. The membrane composition of the present invention may also comprise a coating which may be drug-eluting. The drug-eluting coating may elute compositions such as, for example, drug compositions, antibodies or hormones.

Further, the preferred membrane composition 5 of the present invention may provide for a barrier material with lubricious and low friction surfaces to prevent apposing tissue erosion over long term use. The static coefficient of friction of the preferred membrane compositions 5 may be, for example, about one hundredth (0.01) to about one-half (0.5), preferably about four hundredths (0.04) to about twenty-four hundredths (0.24), more preferably about six hundredths (0.06) to about eighteen hundredths (0.18). The kinetic coefficient of friction of the preferred membrane compositions 5 may be, for example, about one hundredth (0.01) to about one-half (0.5), preferably about four hundredths (0.04) to about twenty-four hundredths (0.24), more preferably about six hundredths (0.06) to about eighteen hundredths (0.18).

In addition, the preferred membrane composition 5 of the present invention may provide for the addition of radiopaque or other color markings within the material to provide a navigation function during re-operations. The membrane composition 5 of the preferred embodiment of the present invention may provide for a covering of sensitive anatomic structures, maintenance of surgical site and/or tissue planes during the healing process and a navigation function during revision surgeries, both by its ability to be used as a plane of dissection and by its ability to be identified through pre-operative x-ray type methods.

The preferred membrane composition 5 of the present invention may have excellent handling properties. Improved handling is desirable for any surgical device but, with a thin and flexible membrane composition 5 of the preferred embodiment, it is preferred that the membrane composition 5 be capable of being laid in place properly and be fastenable to the surrounding structures. The membrane composition 5 of the preferred embodiment of the present invention provides for a thin membrane that is highly flexible and can contour to surfaces preferably without or minimizing bubbling or wrinkling. Further the membrane composition 5 of the preferred embodiment of the present invention may be made thin while maintaining sufficient strength required for fixation due to the combination of filler material or base substrate and gel strength. In addition, the preferred membrane composition 5 of the present invention may have the ability to stretch during placement without creating a highly tensioned construct that could tear after placement.

Embodiments of the present invention may be made semi-transparent allowing the surgeon to visualize structures below the membrane composition 5 during placement.

Membrane compositions 5 of the preferred embodiment of the present invention may have a surface water content that allows for surface tension effects to facilitate ease of flattening and placement prior to fixation. Once sealed in the body this surface water provides a lubricious and low friction surface to the surrounding tissues thus preventing potential complications such as tissue erosion or tissue adhesions. The preferred water content of the membrane composition 5 may be between about fifty percent (50%) and about eighty-five percent (85%), more preferably between about sixty percent (60%) to about eighty percent (80%), more preferably between about sixty-eight percent (68%) to about seventy-five percent (75%). Within this range, the membrane composition 5 has preferred handling characteristics. Lower water content generally leads to stiffer handling and will not contour as easily.

A further embodiment of the present invention may comprise a method of manufacture of the membrane compositions 5 that provides for inking or marking of the textile component 20 in any desired location to assist with the surgical procedure. The ink may be non-radiopaque and used as markers during placement or used as a method to identify the barrier during a re-operation by making the membrane composition 5 a distinct color from the surrounding tissue. Further, the ink may be made radiopaque to allow for specific markings to be included that can help plan a re-operation and locate the membrane composition 5. Additionally, metallic grommets, clips, eyelets or the like may be affixed to the textile component 20 to provide radiopaque marking or a predetermined point of fixation.

The embodiments of the present invention preferably are hydrophilic and synthetic. The membrane compositions 5 of the preferred embodiment of the present invention may be gamma sterilizable and non-absorbable. The preferred membrane compositions 5 of the present invention may have a sufficiently low porosity to prevent tissue in-growth and cellular infiltration, but still allow for the transport of small molecules through the membrane composition 5.

The preferred embodiments of the present invention may be made without any toxic crosslinking agents which provides for a very inert biologic reaction while the membrane composition 5 is implanted in a patient. Further, the preferred membrane compositions 5 of the present invention may be nonabsorbable, permanent, and stable within the body. The membrane compositions 5 of the preferred embodiment of the present invention may be sufficiently flexible to allow for contouring without, or by minimizing, bubbling or wrinkling, thereby providing for smooth placement and can potentially prevent areas or vacuums that can be sites for post-surgical infections.

The preferred embodiments of the present invention may exhibit mechanical properties that contribute to optimum surgical performance. For instance, the membrane composition 5 may be thin and, therefore, unobtrusive to the surrounding anatomy. Even though it may be thin, the membrane composition structure may be sufficiently strong to allow for fixation of the membrane composition 5. The membrane composition 5 may have a thickness range, for example, from about two tenths of a millimeter (0.2 mm) to about three millimeters (3 mm), preferably from about three tenths of a millimeter (0.3 mm) to about one and one-half millimeters (1.5 mm), more preferably from about three tenths of a millimeter (0.3 mm) to about nine tenths of a millimeter (0.9 mm). Thicker membrane compositions 5 could compress vessels or soft tissue. In applications near the esophagus, such configurations could cause dysphasia.

The membrane composition 5 and manufacture of the preferred membrane composition 5 may be modified in different manners to provide for mechanical properties similar to soft tissue located anywhere in the body. In other words, the membrane composition 5 can be tailored to specific performance requirements or preferred characteristics needed in the chosen area of the body. The membrane composition 5 may be resistant to breakdown or delamination. The exposed gel surface of the preferred membrane composition 5 may have sufficiently low friction and be sufficiently lubricious to provide for interaction with adjacent sensitive anatomical structures without causing any tissue erosion or tissue adhesions.

EXAMPLES AND EXPERIMENTS

The following examples and experiments describe some of the properties of the preferred membrane compositions 5 described herein and are only intended to assist in explaining and illustrating certain structures, features and aspects of the membrane composition and not as limiting the scope of the invention to the precise arrangements, compositions, properties or features described.

Example 1

Membrane Composition Formulation and Characterization

A preferred membrane composition 5 comprising a PVA-based hydrogel component 10 with a porous mesh filler component 20 was prepared. The mesh 20 consisted of a fifteen hundredths of a millimeter (0.15 mm) thick knit polyester fabric with medical grade radiopaque ink markings. The PVA-based hydrogel component 10, as described in more detail below, was applied to completely cover the mesh and form the membrane composition 5.

The hydrogel component 10 was created by preparing a twelve and eight tenths percent (12.8%) aqueous polymer solution of PVA and PVP at a 99:1 ratio. At an elevated temperature of approximately eighty degrees Celsius (80° C.), the warm polymer solution was transferred onto the polyester mesh with ink and then drawn over the mesh to form a uniform layer on both sides. The final preferred membrane composition 5 was approximately three tenths of a millimeter (0.3 mm) thick. A process of cyrogelation (i.e., freezing and thawing) was used to create physical crosslinks in the hydrogel component 10. The mesh 20 and ink were encapsulated by the hydrogel component 10 on all sides resulting in a continuous permanent PVA-based hydrogel component. The membrane composition 5 was then packed in a tray with a PBS solution and subjected to gamma sterilization, which further chemically crosslinked the hydrogel component 10. Compositional analysis was performed on the membrane composition 5.

The water content of this preferred membrane composition 5 was determined according to the "Loss on Drying" method as described in the Gravimetric Method from the 2003 United States Pharmacopoeia/National Formulary (USP/NF). Briefly, the membrane composition 5 was heated to one hundred five degrees Celsius (105° C.) to evaporate any water contained in the hydrogel component 10. The mean water content of thirty (30) hydrogel compositions was determined to be seventy-five and three tenths percent (75.3%)±one and eight tenths percent (1.8%).

A mass balance calculation of a one hundred gram (100 g) sample was performed. Table 1 displays the mass of each component.

TABLE 1

| | | Composition analysis of 100 g Sample | | |
|---|---|---|---|---|
| PVA | PVP | Polyester | Water | Total 100 g Sample |
| 10.9 g | 0.1 g | 13.7 g | 75.3 g | 100 g |

The thickness of the membrane composition 5 was measured using a ten ounce (10 oz.) constant load thickness gage according to the method described in "ISO 5084 Determination of Thickness of Textiles and Textile Products" method. A twenty-eight and seven tenths millimeters (28.7 mm) diameter platen was lowered on the test samples. The mean thickness of the thirty hydrogel compositions was thirty-four hundredths of a millimeter (0.34 mm)±three hundredths of a millimeter (0.03 mm).

Example 2

Static and Kinetic Coefficients of Friction of the Membrane Composition

Figure 2:
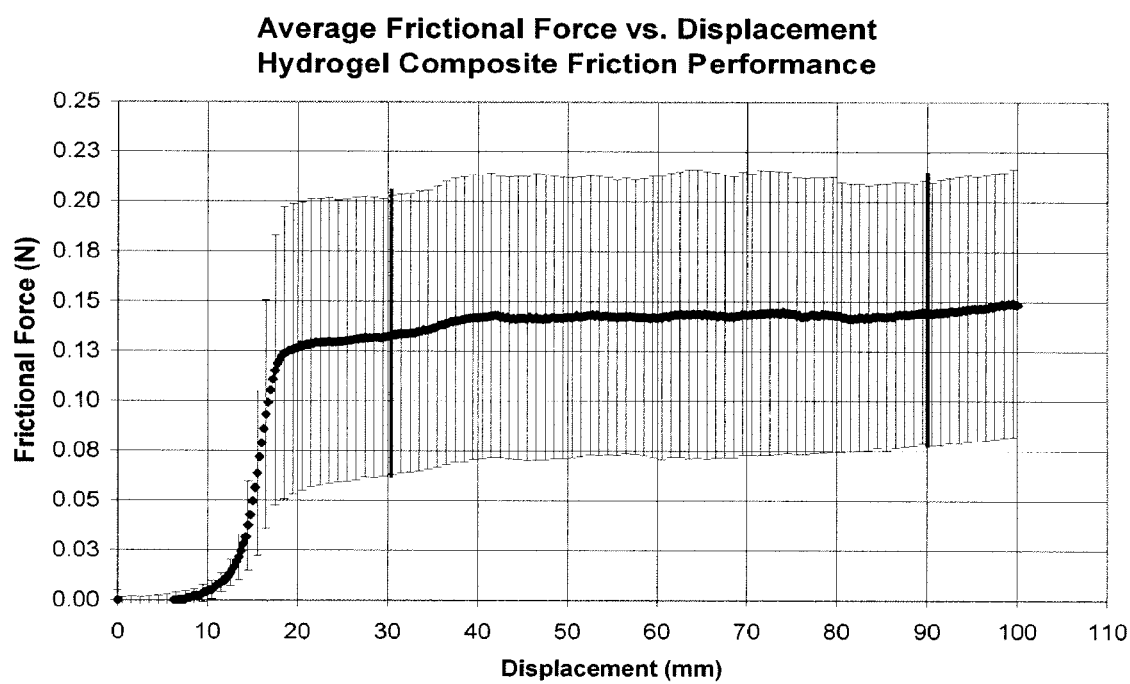
FIG. 2 is a graphical representation of a friction force test of an example of the membrane composition of FIG. 1A.

The static and kinetic coefficients of friction for twenty-four (24) preferred membrane compositions 5 were determined according to the method provided in "ASTM D 1894-06 Standard Test Method for Static and Kinetic Coefficients of Friction of Plastic Film and Sheeting." Briefly, an Instron (model number 3342) with a one hundred Newton (100 N) load cell was used to pull a one hundred thirty-nine and seven tenths grams (139.7 g) sled with the membrane composition 5 attached across a glass surface at a rate of one hundred fifty millimeters per minute (150 mm/min). The test was run at room temperature and moisture was maintained within the specimens throughout the test. See FIG. 2 for a graphical representation of the raw data. The static coefficient of friction was determined to be one hundred thirteen thousandths (0.113)±fifty-three thousandths (0.053). The kinetic coefficient of friction was determined to be one hundred three thousandths (0.103)±fifty-two thousandths (0.052).

Example 3

Suture Strength of the Membrane Compositions

Figure 3:
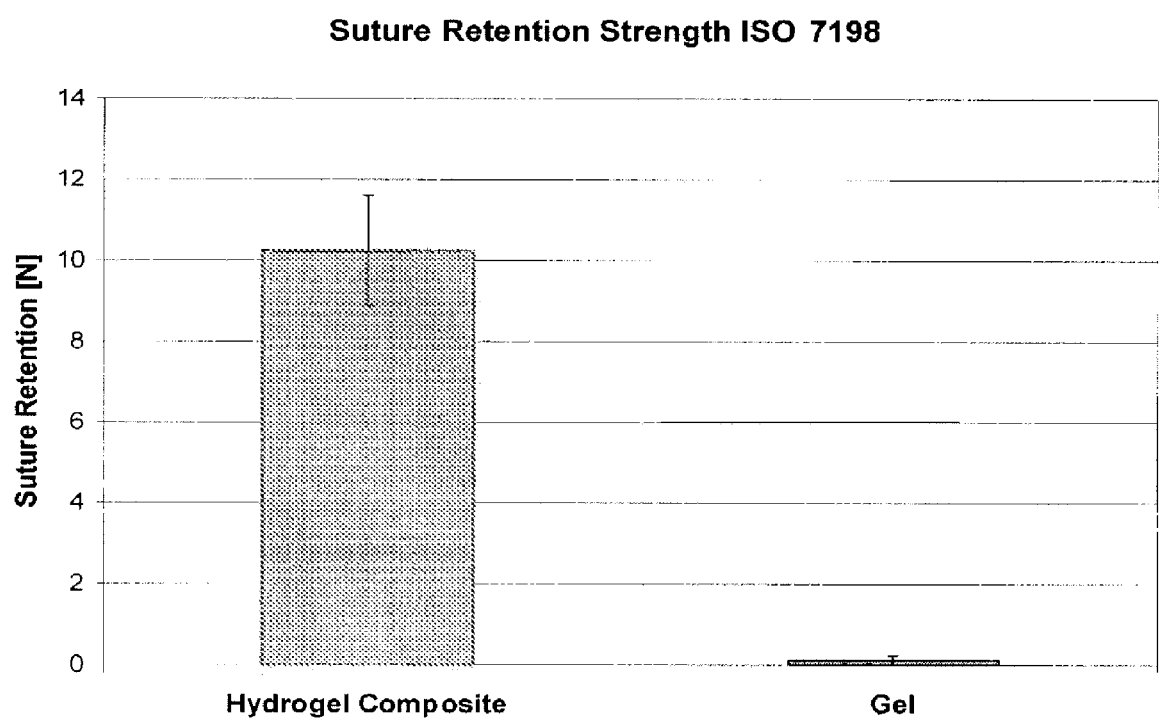
FIG. 3 is a graphical representation of the suture strength of an example of the membrane composition of FIG. 1A.

The suture retention strength of a three tenths of a millimeter (0.3 mm) thick membrane composition and a three tenths of a millimeter (0.3 mm) thick hydrogel component 10 without filler were determined according to ISO 7198 section 8.8 Determination of suture retention strength. Briefly, an Instron (model number 3342) with a 100N load cell was used with a simple tensile test grip apparatus. A 5-0 Prolene Suture with taper point needle was passed two millimeters (2 mm) from the edge of each specimen and formed into a loop and fastened to the top grip of the testing apparatus. The specimen was held with the bottom grip. The Instron was then run at a rate of one hundred millimeters per minute (100 mm/min) until failure. The results of the test are shown in FIG. 3. The membrane composition (n=30) had a mean suture retention strength of ten and five hundredths Newtons (10.05 N)±one and forty-five hundredths Newtons (1.45 N). The hydrogel component 10 alone specimens (n=3) had a mean suture retention strength of twelve hundredths Newtons (0.12 N)±twelve hundredths Newtons (0.12 N). As shown in this example, the matrix filler or base substrate provides a considerable effect with regard to suture retention strength.

Example 4

Tensile Properties of the Membrane Compositions

Figure 4:
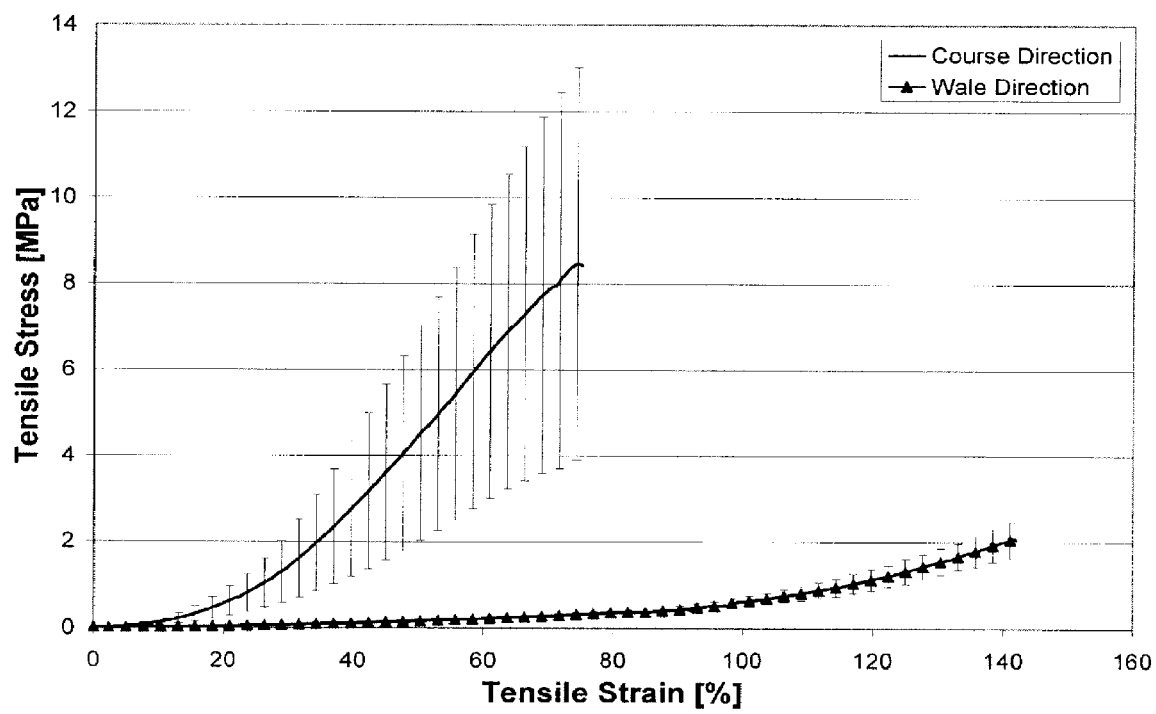
FIG. 4 is a graphical representation of the tensile strength of an example of the membrane composition of FIG. 1A.

Tensile properties of the preferred membrane compositions 5 were determined in two different directions using an Instron (model number 3342). Membrane compositions specimens with dimensions of approximately seventeen millimeters by thirty-eight millimeters by three tenths of a millimeter (17 mm×38 mm×0.30 mm) were created and cut according to the composite mesh knit directions. Six (6) specimens were then tested in the direction of the courses on the fabric and another set of six (6) specimens were tested in the direction of the wales on the fabric. A four hundredths Newton (0.04 N) preload was applied and the specimens were tested at a rate of one hundred millimeters per minute (100 mm/min). The data for both sets is presented in FIG. 4. The membrane compositions 5 were observed to be orthotropic, exhibiting significantly different mechanical behaviors in the two directions evaluated. Further, the membrane compositions 5 exhibit nonlinear behavior and exponential type behavior with large displacements at very low loads followed by a tensioning of the textile filler that leads to sharp increase in load at the large extensions. This behavior is similar to soft tissues in the body. These properties can be adjusted to match or mimic specific soft tissue by adjustments in the hydrogel component 10 and textile component 20 properties. This study demonstrated the ability of the membrane compositions 5 to stretch. The ability to stretch is valuable in surgical applications for handling purposes and to facilitate tension free repairs.

Example 5

Membrane Composition Flexibility

Figure 5:
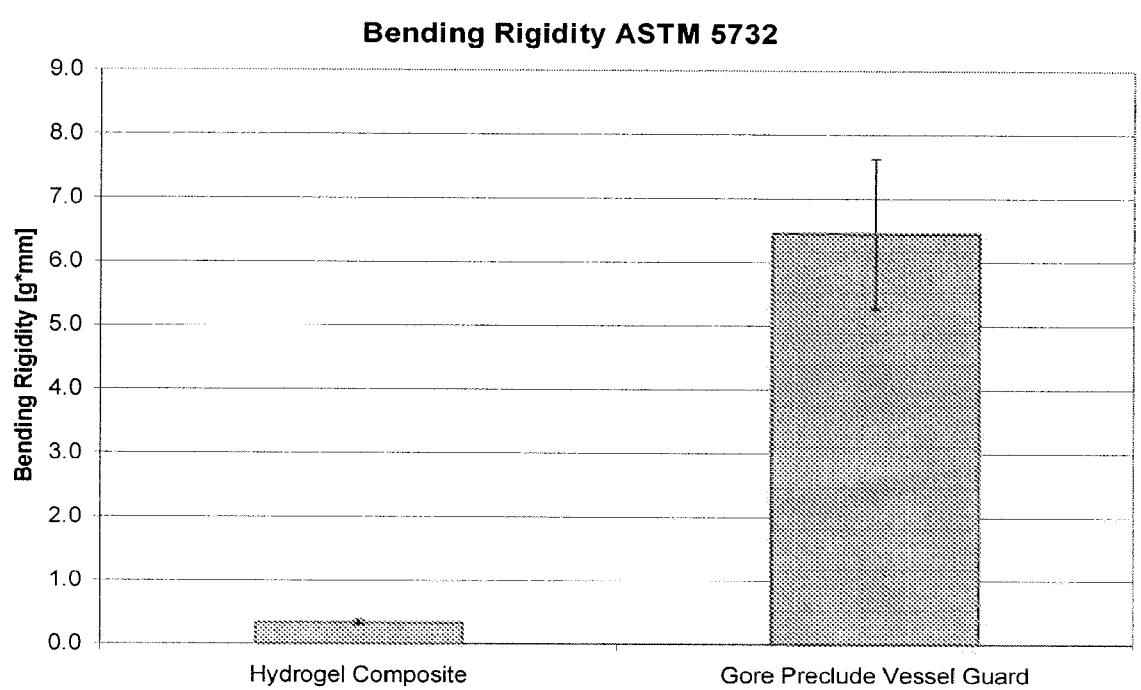
FIG. 5 is a graphical representation of the bending rigidity of an example of the membrane composition of FIG. 1A.

The flexibility of the preferred membrane compositions 5 was compared to an ePTFE sheet using a bending rigidity test apparatus according to ASTM D 5372-95 (Reapproved 2001) Stiffness of Nonwoven Fabrics Using the Cantilever Test. Briefly, the method was a cantilever test in which a specific length and width of the membrane composition 5 specimens was evaluated for bending under its own weight. Bending length was measured as a length of fabric that drapes over an edge and contacts a blade set at forty-one and one-half degrees (41.5°) from the horizontal. A total of sixteen (16) membrane composition 5 specimens were tested and the average bend length was ten millimeters (10 mm)±four tenths of a millimeter (0.4 mm). The ePTFE sheet, a clinically approved device Gore Preclude VesselGuarda with a similar thickness (0.3 mm), was measured in the same test apparatus as a control and the average bend length was twenty-two millimeters (22 mm)±one and four tenths millimeters (1.4 mm). The flexural rigidity of both membranes were calculated according to the standard and determined to be thirty-four (0.34) g·m±four hundredths (0.04) g·m for the membrane composition and six and forty-five hundredths (6.45) g·m±one and seventeen hundredths 1.17 g·m for the ePTFE sheet (results are shown in FIG. 5). The results from this test exemplify the flexibility and pliability of the membrane composition 5 that exhibits minimal flexural rigidity and resistance to bending as compared to the ePTFE sheet. This feature of the membrane composition 5 makes the membrane composition 5 ideal for lying interposed between soft tissues and over metal plates or other implants or instruments. The low stiffness and pliability give the material the ability to drape and contour over other implants or critical structures.

Example 6

Surgical Setting Observations

A surgical setting was created using a human cadaver torso and anterior access instruments with multiple spine and spine access surgeons. The membrane composition 5 was used in the cadaver labs as a cover and protector over an anterior interbody fusion cage, anterior tension band plate, and other anterior access spine procedures. The material properties of the preferred membrane composition 5 enabled it to contour to the spine and the surface of the metal implant, generally without bubbling. In addition, the surface tension of the water in the gel allowed the membrane composition 5 to temporarily stick to the surfaces in the body, the metal implants, and the metal instruments. This helped provide improved handling properties. Since the membrane composition 5 of the preferred embodiment was translucent, it also assisted with placement over the hardware and provided the surgeon visual feedback on the location of important anatomical structures below the membrane 5. The membrane composition 5 contained several radiopaque markings that were visible under fluoroscopy. In addition, the membrane composition 5 was fastened in place using tacks and sutures by the surgeons.

Example 7

Rat Model Studies

Figure 6A:
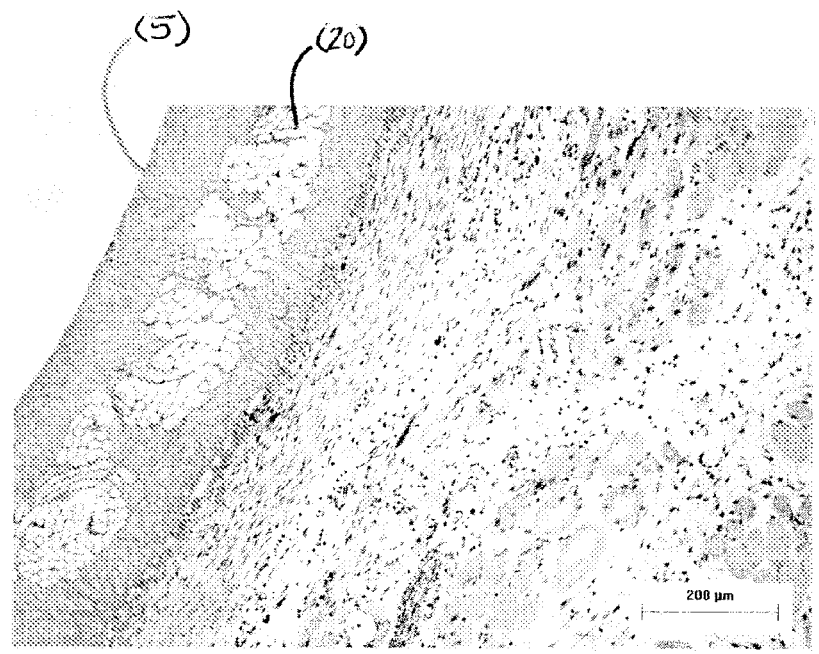
FIGS. 6A and 6B are histological sections of rat tissue containing an example of the membrane composition of FIG. 1A.
Figure 6B:
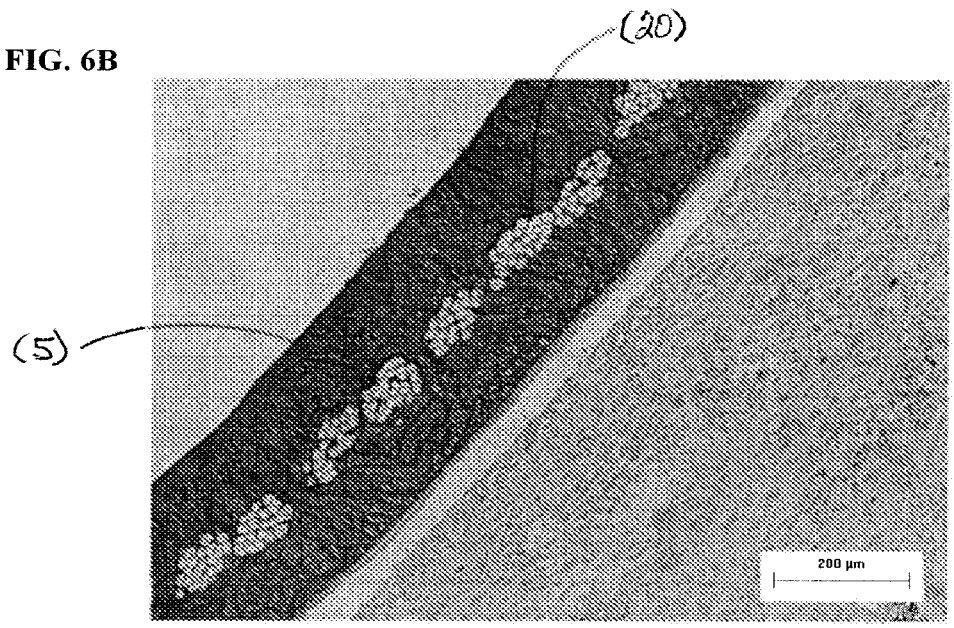

Membrane composition 5 samples of the preferred embodiment were prepared as described in Example 1 with the specified dimensions (1.5 cm×1.0 cm×0.03 cm) and implanted in a rat cecal abrasion model. The desire of the study was to determine if the membrane composition 5 reduced the incidence and severity of adhesions. The study consisted of three groups: 1) a control group with surgical trauma and no barrier (n=13); 2) a clinically approved device Gore Preclude VesselGuard, which is an ePTFE sheet, (n=10); and 3) the preferred membrane composition 5 (n=9). Within a seven day time window, ten of thirteen control animals formed adhesions. A mechanical test was performed to assess the tenacity of these adhesions. The energy absorbed at failure had a mean of twenty-nine and one-half (29.5)±ten and four tenths millijoules (10.4 mJ) and the mean peak load was one and three tenths (1.30)±one-half Newton (0.50 N). Treatment with either the VesselGuard or the membrane composition 5 barrier prevented adhesion formation between the abraded cecum and abdominal wall of the rat over the seven days. There were no strong adhesions to the surface of the membrane composition 5 and histology showed that the gel coating prevents or limits cells from migrating into the mesh. Due to the complete absence of adhesions on the two barrier groups, mechanical testing could not be performed. A thin layer cellular attachment was seen on both barriers evaluated. Histology confirmed a sub-acute to chronic inflammatory response due to the surgical trauma and the absence of tissue in-growth into the preferred membrane composition 5. (See FIG. 6A) Further, Congo red stain was used to identify the hydrogel component 10 and in no case was there evidence that the membrane composition 5 was delaminating or sheared. (See FIG. 6B) In addition, the membrane composition suture fixation remained attached throughout the implantation period. Finally, the VesselGuard is not translucent as is the preferred membrane composition 5. The translucency allows for greater visibility of the structures "behind" the membrane composition 5 once it has been positioned in a patient.

After the study, a histology image was used to determine the maximum pore size within the membrane composition gel matrix. Fifty maximum sized pores were measured digitally from a single three hundred forty by four hundred twenty micrometer (340 µm×420 µm) histology image. The max pore size within the representative area was measured to a mean size of two and seven tenths micrometers (2.7 µm)±nine tenths micrometers (0.9 µm). It is preferred that the size of the pores is less than one hundred micrometers (100 µm) to minimize cellular growth into the membrane composition 5. One function of the hydrogel component 10 is to "fill in" the larger pores of the textile component 20 (as described above).

Example 8

Stability of the Membrane Compositions

Figure 7A:
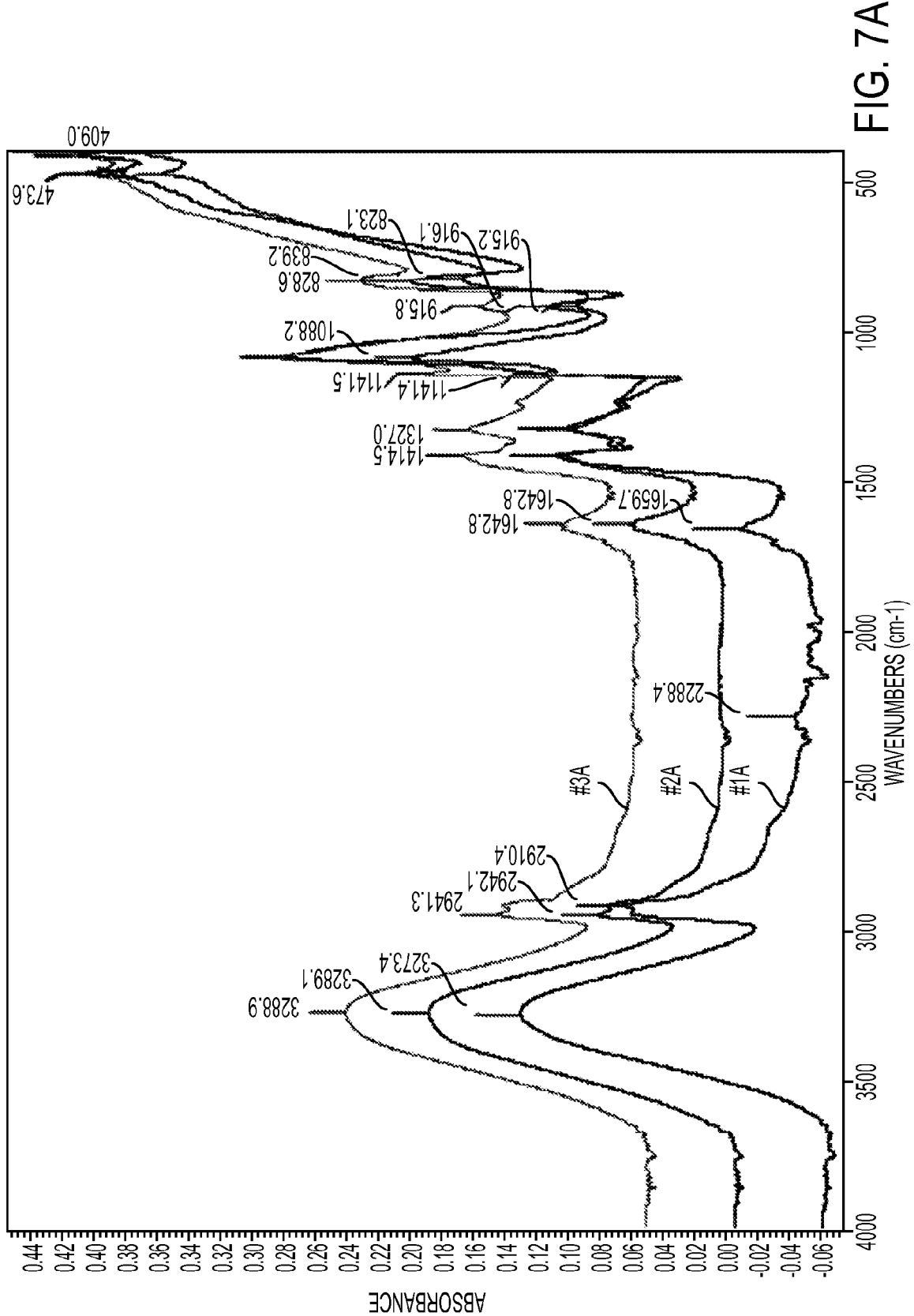
FIG. 7A is a FT-IR spectrum analysis of a pre-conditioned an example of the membrane composition of FIG. 1A.
Figure 7B:
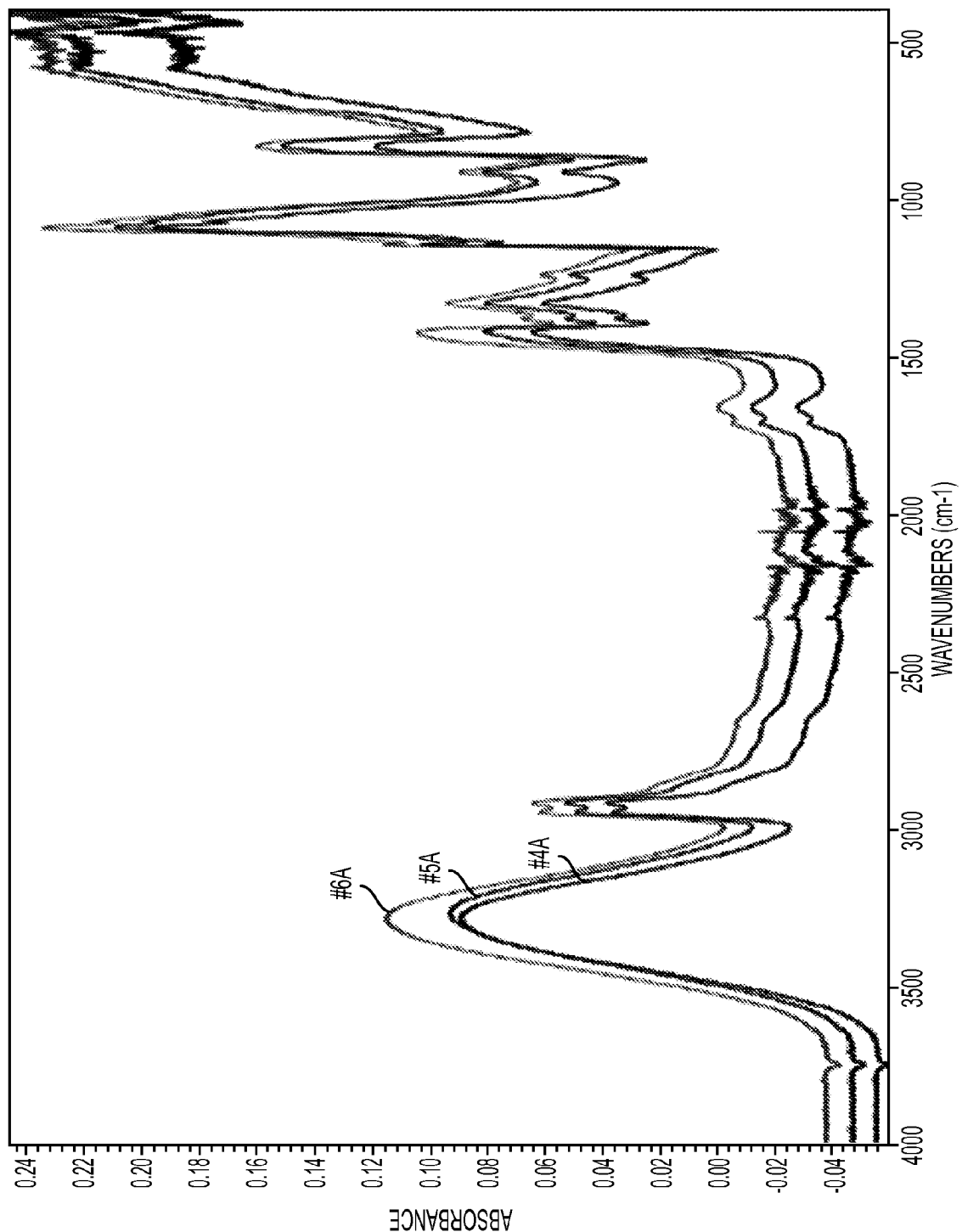
FIG. 7B is a FT-IR spectrum analysis of a post-conditioned an example of the membrane composition of FIG. 1A.

Stability of the preferred membrane composition 5 was evaluated according to the ISO 10993-13 Biological Evaluation of Medical Devices—Identification and Quantification of Degradation Products from Polymeric Medical Devices. Six (6) membrane compositions 5 were labeled 1-6 (1-3 for controls and 4-6 for test samples) and dried overnight at a constant temperature in a vacuum oven. All samples were weighed for dry mass data. Samples 1-3 (controls) were analyzed with Differential Scanning calorimetry (DSC) and Fourier transform spectroscopy (FT-IR) for pre-conditioning thermograms and spectra, while samples 4-6 (test samples) were each put in a glass jar with forty milliliters (40 mL) of deionized (DI) water (following a ratio of one gram (1 g) of sample:forty milliliters (40 mL) of DI water) for seven (7) days. DSC measures changes in heat flow. FT-IR measures chemical bond changes. A stable membrane composition 5 should not have changing bonds or heat flow (i.e., thermograms). Immediately after the immersion in DI water, samples 4-6 were put in a Binder oven set at fifty degrees Celsius (50° C.), monitored and recorded by a Fluke thermometer and thermocouple, for seven (7) days. At the end of seven (7) days, samples 4-6 were taken out of the oven, dried to a constant mass in a vacuum oven for a second time, and weighed for dry mass data. Samples 4-6 were then analyzed with DSC and FT-IR for post-conditioning thermograms and spectra. The residual DI water from the immersion of each implant was filtered (together with an extra ten milliliters (10 mL) rinse water for each jar) using a Glass Microanalysis Filter Holder Assembly. The filter papers were then dried to constant mass and weighed for residual dry mass data. The FT-IR spectrum for samples 1-3 preconditioning and 4-6 post-conditioning are shown in FIGS. 7A and 7B. Although some of the peaks in FIG. 7B (the post-conditioning samples) are of greater intensity than the same peaks in FIG. 7A (the pre-conditioning samples), there are no new peaks in the spectrums for the post-conditioning preferred membrane compositions 5, which would be indicative of degrading polymers. The material balance and analysis showed that the preferred membrane composition 5 was stable and did not break down or dissolve during stability testing. This verified the permanent nature of the membrane composition 5.

The embodiments set forth above, among those made apparent from the preceding description, are efficiently attained and, since certain changes may be made in carrying out the above method of forming and in the resulting composition without departing from the spirit and scope of the invention, it is intended that all material contained in the above description shall be interpreted as illustrative and not in a limiting sense.

It will also be understood that the embodiments presented herein are intended to cover all of the generic and specific features of the composition barrier herein described and all statements of the scope of the invention which, as a matter of language, might be said to fall therebetween. Particularly it is to be understood that in said embodiments, ingredients or compounds recited in the singular are intended to include compatible mixtures of such ingredients.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

The invention claimed is:

1. A membrane for securement to a patient's bone or soft tissue to reduce the formation of tissue adhesions following a surgical procedure comprising a hydrogel including poly(vinyl alcohol) crosslinked to a second polymer, wherein a ratio of the poly(vinyl alcohol) to the second polymer ranges from about 75:1 to about 200:1, wherein the membrane has a static coefficient of friction between about one hundredth (0.01) and about one-half (0.5), a kinetic coefficient of friction between about one hundredth (0.01) and about one-half (0.5), and flexibility of less than thirty millimeters (30 mm) bend length, and wherein the membrane is formed into a single, planar sheet.

2. The membrane of claim 1, wherein the second polymer is selected from the group consisting of poly(vinyl pyrrolidone), poly(hydroxyethylmethacrylate), poly(acrylamide), poly(acrylic acid), poly(acrylonitrile), polyethylene imine and poly(ethylene glycol).

3. The membrane of claim 1, wherein the second polymer is poly(vinyl pyrrolidone).

4. The membrane of claim 1, wherein the ratio ranges from about 75:1 to about 110:1.

5. The membrane of claim 1, wherein the poly(vinyl alcohol) and the second polymer are crosslinked by a method selected from the group consisting of cryogelation, dehydration processing, radiation and exposure to chemicals.

6. The membrane of claim 1, wherein the membrane has a thickness between about two tenths of a millimeter (0.2 mm) to about three millimeters (3 mm).

7. The membrane of claim 1, wherein the membrane has a thickness between about three tenths of a millimeter (0.3 mm) to about one and one-half millimeters (1.5 mm).

8. The membrane of claim 1, further comprising radiopaque markings.

9. A membrane composition for securement to a patient's bone or tissue comprising a hydrogel including poly(vinyl alcohol) and a second polymer selected from the group consisting of poly(vinyl pyrrolidone), poly(hydroxyethylmethacrylate), poly(acrylamide), poly(acrylic acid), poly(acrylonitrile), polyethylene imine and poly(ethylene glycol), wherein the poly(vinyl alcohol) and the second polymer are crosslinked and a ratio of the poly(vinyl alcohol) to the second polymer ranges from about 75:1 to about 200:1, wherein the composition has sufficient thickness, lubricity and flexibility to reduce the formation of tissue adhesions following a surgical procedure, and wherein the composition is formed into a single, planar sheet configured to adhere to the patient's spine to provide a plane of dissection between the spine and tissue.

10. The composition of claim 9, wherein the second polymer is poly(vinyl pyrrolidone).

11. The composition of claim 9, wherein the ratio ranges from about 75:1 to about 110:1.

12. The composition of claim 9, wherein the poly(vinyl alcohol) and the second polymer are crosslinked by a method selected from the group consisting of cryogelation, dehydration processing, radiation and exposure to chemicals.

13. The composition of claim 9, wherein the composition has a thickness between about two tenths of a millimeter (0.2 mm) to about three millimeters (3 mm).

14. The composition of claim 9, wherein the composition has a thickness between about three tenths of a millimeter (03 mm) to about one and one-half millimeters (1.5 mm).

15. The composition of claim 9, further comprising radiopaque markings.

16. The composition of claim 9, wherein the composition has a water content between about fifty percent (50%) and about eighty-five percent (85%).

17. A membrane for use as a surgical implant comprising: a hydrogel including poly(vinyl alcohol) and poly(vinyl pyrrolidone), wherein a ratio of the poly(vinyl alcohol) to the poly(vinyl pyrrolidone) is between about 75:1 and about 200:1, wherein the membrane has a thickness between about three tenths of a millimeter (0.3 mm) and about one and one-half millimeters (1.5 mm), wherein the poly(vinyl alcohol) and the poly(vinyl pyrrolidone) are crosslinked by cryogelation, wherein the membrane has a water content between about sixty-eight percent (68%) and about seventy-five percent (75%).

18. The membrane of claim 17, wherein the ratio is between about 75:1 and about 110:1.

* * * * *